(12) United States Patent
Zhu et al.

(10) Patent No.: US 12,085,566 B2
(45) Date of Patent: *Sep. 10, 2024

(54) **INERT CARRIER *SALMONELLA* AND POTENTIAL USE THEREOF**

(71) Applicant: YANGZHOU UNIVERSITY, Yangzhou (CN)

(72) Inventors: Guoqiang Zhu, Yangzhou (CN); Bin Yang, Yangzhou (CN); Pengpeng Xia, Yangzhou (CN); Qiangde Duan, Yangzhou (CN); Yang Yang, Yangzhou (CN); Xia Meng, Yangzhou (CN); Xiaofang Zhu, Yangzhou (CN)

(73) Assignee: YANGZHOU UNIVERSITY, Yangzhou (CN)

( * ) Notice: Subject to any disclaimer, the term of this patent is extended or adjusted under 35 U.S.C. 154(b) by 751 days.

This patent is subject to a terminal disclaimer.

(21) Appl. No.: 16/963,079

(22) PCT Filed: Jan. 13, 2020

(86) PCT No.: PCT/CN2020/071626
§ 371 (c)(1),
(2) Date: Jul. 17, 2020

(87) PCT Pub. No.: WO2020/233148
PCT Pub. Date: Nov. 26, 2020

(65) Prior Publication Data
US 2022/0003763 A1 Jan. 6, 2022

(30) Foreign Application Priority Data
May 21, 2019 (CN) .......................... 201910424369.8

(51) Int. Cl.
*G01N 33/569* (2006.01)
*C12N 1/20* (2006.01)
*C12R 1/42* (2006.01)

(52) U.S. Cl.
CPC ....... *G01N 33/56916* (2013.01); *C12N 1/205* (2021.05); *C12R 2001/42* (2021.05); *G01N 2333/255* (2013.01)

(58) Field of Classification Search
CPC ....... G01N 33/56916; G01N 2333/255; G01N 33/554; C12N 1/1205; C12R 2001/42
See application file for complete search history.

(56) References Cited

PUBLICATIONS

Penner, J. L., and JN273687 Hennessy. "Passive hemagglutination technique for serotyping *Campylobacter fetus* subsp. *jejuni* on the basis of soluble heat-stable antigens." Journal of clinical microbiology 12.6 (1980): 732-737. (Year: 1980).*

(Continued)

*Primary Examiner* — Louise W Humphrey
*Assistant Examiner* — Candice Lee Swift
(74) *Attorney, Agent, or Firm* — JCIPRNET

(57) ABSTRACT

The present invention relates to an inert carrier *Salmonella* and potential use thereof, which is expected to be developed into a new inert carrier bacteria, and can be applied to the development of an indirect agglutination test method for simple and rapid detection of antigens or infected antibodies. The inert carrier *Salmonella* has been deposited in CGMCC in Beijing on Mar. 18, 2019 with the accession number of CGMCC No.17340, and is classified as *Salmonella sp.* with a strain code of S9. The *Salmonella* has no visible agglutination reaction with various chicken sera derived from different genetic backgrounds, i.e., it has no non-specific agglutination reaction with chicken sera derived from broad range of genetic backgrounds.

2 Claims, 2 Drawing Sheets
Specification includes a Sequence Listing.

(56) References Cited

PUBLICATIONS

Li, Wenjun, Didier Raoult, and Pierre-Edouard Fournier. "Bacterial strain typing in the genomic era." FEMS microbiology reviews 33.5 (2009): 892-916. (Year: 2009).*

Tamura, Hiroto, Yudai Hotta, and Hiroaki Sato. "Novel accurate bacterial discrimination by MALDI-time-of-flight MS based on ribosomal proteins coding in S10-spc-alpha operon at strain level S10-GERMS." Journal of The American Society for Mass Spectrometry 24.8 (2013): 1185-1193. (Year: 2013).*

Stackebrandt, Erko, et al. "Deposit of microbial strains in public service collections as part of the publication process to underpin good practice in science." SpringerPlus 3.1 (2014): 1-4. (Year: 2014).*

Zhang, Jiang-ying, et al. "Simple and rapid detection of *Salmonella* by direct PCR amplification of gene fimW." Current microbiology 69.4 (2014): 429-435. (Year: 2014).*

Witkowska, Evelin, et al. "Strain-level typing and identification of bacteria—a novel approach for SERS active plasmonic nanostructures." Analytical and bioanalytical chemistry 410.20 (2018): 5019-5031. (Year: 2018).*

CGMCC catalogue; https://www.cgmcc.net/english/catalogue; accessed Dec. 8, 2022 (Year: 2022).*

Korhonen, Timo K., Hakon Leffler, and Catharina Svanborg Edén. "Binding specificity of piliated strains of *Escherichia coli* and *Salmonella typhimurium* to epithelial cells, *Saccharomyces cerevisiae* cells, and erythrocytes." Infection and Immunity 32.2 (1981): 796-804. (Year: 1981).*

Tamada et al. J Clin Microbiol. Mar. 2001;39(3):1057-66. doi: 10.1128/JCM.39.3.1057-1066.2001. PMID: 11230427; PMCID: PMC87873. (Year: 2001).*

Pérez-Sotelo, Luis Salvador, et al. "In vitro evaluation of the binding capacity of *Saccharomyces cerevisiae* Sc47 to adhere to the wall of *Salmonella* spp." Rev Latinoam Microbiol 47.3-4 (2005): 70-75. (Year: 2005).*

Zhang, Jiang-ying, et al. "Simple and rapid detection of *Salmonella* by direct PCR amplification of gene fimW." Current microbiology 69 (2014): 429-435. (Year: 2014).*

National Veterinary Institute; https://www.sva.se/en/what-we-do/feed-safety/general-facts-about-salmonella/salmonella-in-poultry/#:~:text=Salmonella%20Pullorum%20and%20Salmonella%20Gallinarum%20are%20especially%20adapted%20to%20poultry, Gallinarum).; accessed Nov. 30, 2023 (Year: 2020).*

* cited by examiner

INERT CARRIER *SALMONELLA* AND POTENTIAL USE THEREOF

TECHNICAL FIELD

The present invention belongs to the field of biomedical detection, and relates to a *Salmonella* with inert carrier characteristics, and isolation, identification and potential use thereof. It reveals the characteristics that the bacteria number of the inert carrier *Salmonella* at a working concentration has no non-specific agglutination reactions with various chicken sera derived from different genetic backgrounds, thus an isolated strain from the inert carrier *Salmonella* can be used as an inert carrier bacteria, and has potential use prospects in the development of an indirect agglutination test method for simple and rapid detection of antigens or infected antibodies.

BACKGROUND

The agglutination test is a classic rapid immunological diagnosis method which is widely used in medicine and veterinary clinics, and its principle is that after the insoluble particle antigens such as bacteria and red blood cells are bound to the corresponding antibodies at the presence of an electrolyte, the antigen particles will agglomerate and aggregate with each other, forming small aggregates or particles that are visible to naked eyes. The antigen involved in the reaction is called agglutinogen, and the antibody is called lectin. Plate agglutination test is a more widely used qualitative method in the agglutination reaction. A drop of a diagnostic serum (containing a known antibody) and a drop of the bacteria suspension to be tested are dropped on a clean transparent glass plate, and gently mixed in equal volume. Waiting for 2 minutes at room temperature, if there is particle agglutination visible to naked eyes, it is a positive agglutination reaction, which is often used for identification of bacteria, serotyping and the like. In turn, known diagnostic antigens can also be used to detect the presence of corresponding antibodies in the serum or whole blood to be detected, and are commonly used in the glass plate agglutination reaction for the diagnosis of *Brucella* infection and the whole blood plate agglutination test for *Salmonella pullorum/typhimurium* and the like in veterinary clinics. It is worth noting that with the improvement and development of agglutination tests, in some studies, specific antigen molecules are coated in latex particles and other inert carriers to detect serum antibodies. The indirect agglutination reaction technology developed on the basis of the direct agglutination reaction has expanded the detection application range and increased the sensitivity of the reaction.

The agglutination test is suitable for the rapid diagnosis of some pathogenic infections. It has many advantages such as simple and fast, no additional equipment, no expensive equipment, low cost and detection on site, but in practice, some drawbacks and technical bottlenecks have appeared, for example, taking the detection of the whole blood plate agglutination antigens infected with *Salmonella pullorum/typhimurium* as an example, the agglutination antigen detection has certain limitations in practice applications. It has been reported that there are a variety of obvious cross non-specific reactions of diagnostic antigens, inconsistent detection results of each batch, poor repeatability, weak positives, poor sensitivity, missed detections and other factors that affect the detection results, and the method is only relatively sensitive to the detection effect of adult flocks rather than younger chickens, and there may be large missed detection errors for chicks. For the preliminary study data from the same laboratory located, the same technical person used commercially available *Salmonella pullorum/typhimurium* stained agglutination antigen to detect the same batch of 200 serum samples from a chicken farm twice at different times, it was found that the total coincidence rate of the detection results for two batches of samples was only 81%, indicating that the test results of each batch are not stable and consistent. When comparing the detection results with the *Salmonella* D group ELISA kit of BioChek in the Netherlands, it was found that the total coincidence rate of the detection results was only 79.5%, the positive coincidence rate (detection rate or sensitivity) was 75.2-79.4%, and the negative coincidence rate was 79.5-85.5%. The above detection results and comparative analysis showed that when the commercial agglutination antigen was used to detect the *Salmonella pullorum/typhimurium* serum antibody, the sensitivity, specificity, repeatability, stability and accuracy of the results did not reach a level to be desired, indicating that there was a certain degree or more obvious false positive misdetection and false negative missed detection in the results of the commercial agglutination antigens being used.

The fundamental reason why the accuracy of the agglutination antigen test results needs to be improved is that the agglutination antigens currently used in the agglutination test are whole bacterial antigens which are bacterial particle antigens with multiple antigen components, rather than single somatic antigen of O1, O9, and O12. In theory, this whole bacterial antigen with multiple antigen components will have homology and the same components as bacteria of the same family, same genera and other different genera (especially in Enterobacteriaceae), which will produce non-specific cross-reactions to a certain extent. It is worth noting that, in view of the fact that the working concentration of the agglutination antigen contains a higher concentration of bacteria, easily resulting in non-specific cross-reaction and this non-specific cross-reaction disadvantage will inevitably affect or even significantly interfere with the detection and diagnosis results, thereby seriously affecting the epidemic eradication effect and the advancement of epidemic eradication work, particularly for test and cull of vertical transmission diseases such as *Salmonella pullorum* infection of the poultry industry.

Therefore, if a specific inert carrier bacteria capable of carrying and expressing a single antigen is used to replace the whole bacterial antigen with multiple antigen components as the agglutination antigen, while preserving the advantages of intuitive agglutination reaction results, easy operation and the like, it can accurately and perfectly improve the specificity and sensitivity of the agglutination antigen reaction, effectively improve on-site rapid diagnosis methods for some pathogen infections, and has huge application prospects.

SUMMARY

Objective of the invention: in view of the urgent need to improve and perfect the specificity, sensitivity, repeatability, stability and accuracy of test results of the current rapid diagnostic technology for detecting pathogenic infections (agglutination test) in medicine and veterinary clinics, in the present invention we isolated and identified a *Salmonella* strain with the inert carrier characteristics, which has no non-specific agglutination reaction with different kinds of chicken sera. It is expected to provide an inert carrier bacteria and potential use thereof in the development of a simple and rapid indirect agglutination detection method.

Technical solution: in order to solve the problems in the existing technology, the present invention adopts the following technical solutions: an inert carrier *Salmonella* S9, which has been deposited in the China General Microbiological Culture Collection Center (CGMCC) on Mar. 18, 2019 with the accession number of CGMCC No. 17340, and is classified as *Salmonella* with a strain code of S9.

The carrier bacteria (i.e., the inert carrier *Salmonella*) can be cultured in LB or XLD agar medium, and the cultivation method is as follows: picking a small amount of the stored strains and marking on LB or XLD agar medium, and cultivating at 37° C., wherein gray-white round colonies can be formed after cultivation at 37° C. in the LB agar plate; pink round colonies without metallic luster can be formed after cultivation at 37° C. in the XLD agar plate.

According to the national standard method (GB 4789.4-2016) for *Salmonella* isolation and identification, a strain of chicken-derived *Salmonella* is isolated clinically (healthy chicken flock) according to the national standard method, and the PCR primers targeting *Salmonella* species-specific fimW gene is used to identify the *Salmonella* carrier strain S9. PCR amplification result is consistent with that of the standard *Salmonella typhimurium* U20 strain. A biochemical test is used to biochemically identify the carrier bacteria, and the result is consistent with that of the standard *Salmonella typhimurium* U20 strain.

The glass plate agglutination test is used to verify that the carrier bacteria (i.e., the inert carrier *Salmonella*) suspension does not have self-coagulation phenomenon, and has no non-specific agglutination reactions with various genetic types of chicken sera derived from different genetic backgrounds. The chicken sera include, but are not limited to, SPF chicken serum, healthy chicken serum, chicken bacterial infection positive serum (e.g., avian *Salmonella* positive serum, *E. coli* positive serum, *Staphylococcus* positive serum, *Pasteurella* positive serum and the like), chicken parasite infection positive serum (e.g., chicken coccidiosis positive serum, taeniasis positive serum and the like), chicken viral infection positive serum (e.g., Chicken Newcastle disease positive serum, avian influenza positive serum, chicken Marek's disease positive serum, chicken infectious bursal disease positive serum, chicken egg drop syndrome positive serum, avian encephalomyelitis virus infection positive serum and the like) and various kinds of immunized chicken sera derived from different genetic backgrounds, of which the detected agglutination results are negative.

The bacteria number of the inert carrier *Salmonella* at the working concentration does not produce non-specific agglutination reaction with SPF chicken serum infected with *Salmonella gallinarum*, SPF chicken serum infected with *Salmonella enteritidis*, and the standard *Salmonella typhimurium* U20 strain, *Salmonella pullorum* CVCC535 (China Veterinary Microbial Culture Collection Management Center), *Salmonella enteritidis* 50336 strain and the like can all react with the above SPF chicken serum infected with *Salmonella gallinarum*, and SPF chicken serum infected with *Salmonella enteritidis*.

The summary of the present invention further includes use of the inert carrier *Salmonella* as an inert carrier in an indirect agglutination test for detecting antigens or antibodies, because the inert carrier bacteria S9 is an insoluble particle antigen, and has the function of an indirect agglutination test carrier and inert carrier.

The summary of the present invention further includes use of the inert carrier *Salmonella* as a reagent in an indirect agglutination test for detecting antigens or antibodies, because the inert carrier bacteria S9 can be used as an inert carrier for an indirect agglutination test for detecting antigens or antibodies, and can also be used as a reagent in an indirect agglutination test for detecting antigens or antibodies.

The summary of the present invention also includes use of the inert carrier *Salmonella* as a reagent, technique and platform for detecting a chicken-related pathogen infection, because the inert carrier bacteria S9 can be used in an indirect agglutination test for detecting antigens or antibodies, and can also be used for detecting chicken-related pathogen infections (antibodies).

Compared with the prior art, the advantages of the present invention are:

The present invention provides a *Salmonella* isolated strain S9 with inert carrier characteristics, and its higher bacteria number at a working concentration has no agglutination reaction with different kinds of chicken sera. Based on the inert carrier bacteria has the properties of expressing and presenting antigens on the bacterial surface, it can be used to the development of an indirect agglutination test method for simple and rapid detection of antigens or infected antibodies. It innovatively improves and perfects the specificity and sensitivity bottleneck of the agglutination test in the existing agglutination antigen antibody detection, and has great application value and market prospects.

An inert carrier *Salmonella*, having a strain code is S9, which has been deposited in the China General Microbiological Culture Collection Center (CGMCC) in Beijing on Mar. 18, 2019 with the accession number of CGMCC No. 17340, and is classified as *Salmonella* sp.

Figure 2:
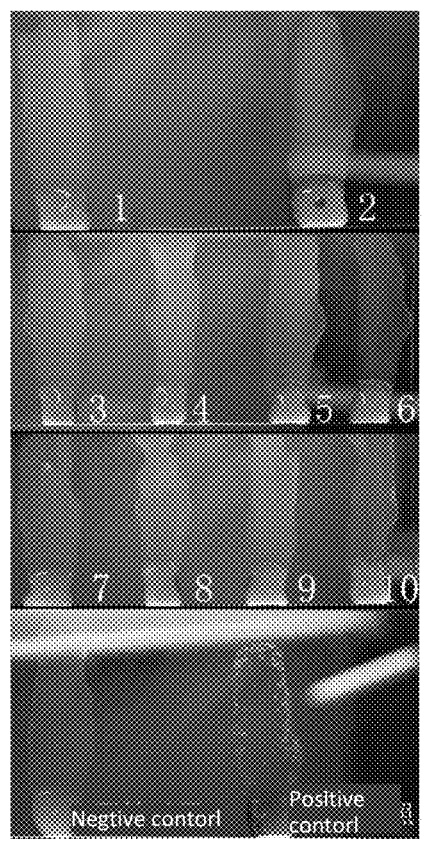

FIG. 2 is the test results diagram of the agglutination reaction of the carrier S9 bacteria suspension with a bacteria concentration of 10 billion CFU/mL and various chicken sera of different genetic backgrounds:

1: SPF chicken serum; 2: Infected chicken positive serum (avian *Salmonella* positive serum); 3: Infected chicken positive serum (*Salmonella* positive serum); 4: Infected chicken positive serum (chicken coccidiosis positive serum); 5: Infected chicken positive serum (taeniasis positive serum); 6: Viral infected chicken positive serum (chicken Newcastle disease positive serum); 7: Viral infected chicken positive serum (chicken Newcastle disease positive serum); 8: Viral infected chicken positive serum (avian influenza positive serum); 9: Vaccinated yellow feather type of local breed broiler serum; 10: Vaccinated Guangxi Yuanfeng-based Lingshan fragrant chicken breed broiler serum.

Note: the negative control for agglutination reaction is the reaction between S9 and physiological saline; the positive control for agglutination reaction is the agglutination reaction between the *Salmonella pullorum* reference strain CVCC526 and the SPF chicken positive serum infected with *Salmonella enteritidis*.

DETAILED DESCRIPTION

The present invention will be further described in detail below in conjunction with specific embodiments.

Before further describing the specific embodiments of the present invention, it should be understood that the protection scope of the present invention is not limited to the following specific embodiments; it should also be understood that the terms used in the embodiments of the present invention are to describe specific embodiments, not to limit the protection scope of the present invention. Unless otherwise defined, all technical and scientific terms used in the present invention have the same meaning as commonly understood by those skilled in the art. In addition to the specific methods, equipment, and materials used in the embodiments, based on the knowledge of the prior art and the description of the present invention by those skilled in the art, any method, equipment and material of the prior art that is similar to or equivalent to the method, equipment and material in the embodiments of the present invention can also be used to achieve the present invention.

Example 1: Isolation and Identification of Salmonella S9

Figure 1:
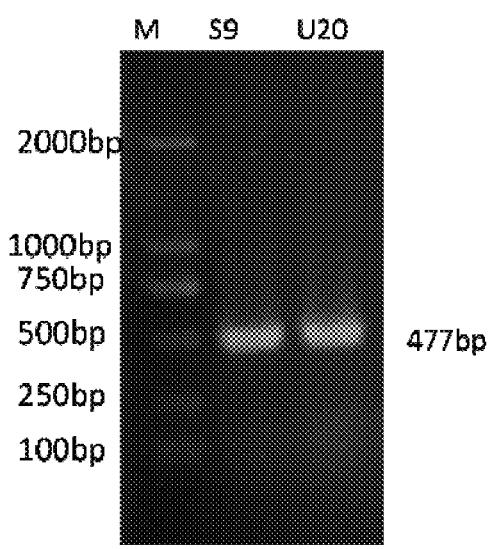
FIG. 1 is the identification results of specific primer for *Salmonella* fimW.

360-day-old healthy laying hens were collected from healthy chicken flocks of the buildings 2 and 4 in the first poultry farm of Jiangsu Wuxi Mashan Poultry Group on Oct. 18, 2016, and placed in ultra-clean benches. The pre-haired chicken body surface was sterilized with alcohol, and chicken's liver, spleen, intestine and other organs and tissues were collected aseptically, placed in a sterile culture dish, and ground thoroughly. Homogenate was drawn into a sterile test tube, and added into buffered peptone water (BPW) to for shaking culture at 37° C. overnight. 1 mL of the culture solution was drawn and inoculated in selenite cystine broth (SC) for selective culture. The broth was drawn with the inoculation loop, and streak inoculated on the xylose lysine deoxycholate (XLD) plate, which was placed in a 37° C. incubator overnight, and suspicious colonies were selected. The isolated strain were identified using the reported primer of fimW for Salmonella species. 1 mL of the above bacteria solution cultured overnight was taken to prepare a DNA template by a boiling method. PCR was used to amplify the fimW DNA fragment, and it was observed and identified by 1.5% gel electrophoresis, and the expected size of the target DNA fragment was 477 bp; the synthetic primer sequences in reference were as follows: fimW-F: 5'AACAGTCACTIT-GAGCATGGGTT 3' (SEQ ID NO.1); fimW-R: 5'GAGTGACTTTGTCTGCTCTTCA 3' (SEQ ID NO. 2); the reaction system 20 μL, including 10 μl of 2× Taq Master Mix (Dye Plus), each 1 μL of fimW-F/R(10 μM), 2 μL of DNA template, 6 μl of sterile ultrapure water to make up 20 μL; the PCR reaction conditions: 94° C. for 5 min; 94° C. for 30 s, 60° C. for 30 s, 72° C. for 30 s, 30 cycles; 72° C. for 10 min. The results showed that the isolated strain was able to amplify the fimW fragment band of the same size as the reference U20 strain of Salmonella gallinarum (FIG. 1).

The isolated strain and single colonies of Salmonella gallinarum U20 strain were inoculated in liquid LB broth at 37° C. with shaking overnight for serotype comparison; sucrose, lactose, comparison of glucose, raffinose, maltose, mannitol, indole, mannose, citric acid, dulcitol, ornithine, lysine, potassium cyanide, hydrogen sulfide, urea, ONPG, MR test, V-P test, semi-solid agar, Adonis amurensis, nitrate reduction, and other trace biochemical reactions.

Table 1 showed the comparison of the biochemical characteristics of the isolated strain and the reference strain U20 of Salmonella gallinarum. The results showed that the biochemical test results of the two strains were consistent.

The above results indicated that we isolated and identified a type of Salmonella strain and named it S9.

TABLE 1

The comparison of biochemical characteristics of carrier strain S9 and reference strain U20 of Salmonella gallinarum

| Strain | Sucrose | Lactose | Glucose | Raffinose | Mannose | Maltose | Mannitol | Citric acid | Dulcitol | Ornithine |
|---|---|---|---|---|---|---|---|---|---|---|
| S9 | − | − | + | − | + | + | + | − | − | − |
| U20 | − | − | + | − | + | + | + | − | − | − |

| Strain | Lysine | Potassium cyanide | Hydrogen sulfide | Indole | Urea | ONPG | MR | VP | Semi-solid agar | Adonis amurensis | Nitrate reduction |
|---|---|---|---|---|---|---|---|---|---|---|---|
| S9 | + | − | + | − | − | − | + | − | − | − | + |
| U20 | + | − | + | − | − | − | + | − | − | − | + |

Note:
"−" represents negative; "+" represents positive.

Example 2 Verification that Inert Salmonella S9 has No Non-Specific Agglutination with Different Kinds of Chicken Sera Derived from Genetic Background The inert carrier bacteria S9 was inoculated into LB liquid medium and shaken overnight, and was centrifuged at 4° C. with a centrifuge at 4000 rpm for 10 min the next day. The supernatant was discarded. The bacteria pellet was resuspended in sterile PBS and washed three times before being resuspended to different concentrations of bacteria (500 million to 10 billion cfu/mL) quantity gradient. Before test, the bacteria solution was mixed with a vortexer, and the agglutination test was first performed with sterile PBS/ normal saline and SPF chicken sera to ensure that the bacteria solution had no self-coagulation and non-specific agglutination. A few pieces of surface-cleaned ordinary glass plates were taken in a clean table (room temperature, 20-25° C.), the carrier bacteria was centrifuged, resuspended and washed with sterile PBS pre-cooled to 4° C. for 3 times, and then resuspended and diluted to the specified bacteria concentration. A drop (approximately 10 μL) of carrier bacteria was drawn and dropped vertically on the surface of a glass plate placed horizontally.using a micropipette. Then an equal amount of serum to be tested was quickly added. The bacteria solution and serum were mixed thoroughly by using a sterilized pipette tip, and coated into a sheet with a diameter of 1-2 cm, and then the glass plate was shaken smoothly. The test results must be observed within 2 min. The standard judgment status was that within 2 min at room temperature, if the bacteria solution and the serum to be tested produced a flocculent or granular precipitate visible to naked eyes, the reaction result was judged as agglutination reaction positive, otherwise it was judged as negative.

The results showed that under different concentration conditions (500 million to 10 billion cfu/mL), the inert *Salmonella* carrier strain S9 had no self-coagulation, and the results of agglutination tests with different types of chickens from different backgrounds, including: SPF chicken serum, chicken bacterial infection positive serum, chicken parasite infection positive serum, chicken virus infection positive serum and multiple immunized chicken sera, were all negative (Table 2 and FIG. 2), indicating that the inert *Salmonella* S9 had no non-specific agglutination reaction with different kinds of chicken sera at high concentration of bacteria, and it can be used as an inert carrier bacteria.

TABLE 2

Agglutination reaction test results of different concentrations of carrier bacteria S9 suspension with chicken sera

| | Carrier bacteria S9 bacteria suspension with different concentrations (cfu/mL) | | | | |
|---|---|---|---|---|---|
| | 500 million | 1 billion | 2 billion | 5 billion | 10 billion |
| SPF Chicken Serum (provided by Shandong Agricultural University) | − | − | − | − | − |
| SPF Chicken Serum (provided by Harbin Medical University) | − | − | − | − | − |
| Avian *Escherichia coli* positive serum | − | − | − | − | − |
| Avian *Escherichia coli* clinical negative serum | − | − | − | − | − |
| SPF chicken serum infected with O1 *Escherichia coli* | − | − | − | − | − |
| SPF chicken serum infected with O2 *Escherichia coli* | − | − | − | − | − |
| SPF chicken serum infected with O78 *Escherichia coli* | − | − | − | − | − |
| *Salmonella* clinical positive serum | − | − | − | − | − |
| SPF chicken serum infected with *Salmonella gallinarum* | − | − | − | − | − |
| SPF Chicken serum infected with *Salmonella enteritidis* | − | − | − | − | − |
| *Salmonella pullorum/typhimurium* clinical positive serum | − | − | − | − | − |
| *Salmonella pullorum/typhimurium* clinical negative serum | − | − | − | − | − |
| Avian Pasteurellosis positive serum | − | − | − | − | − |
| Chicken *Staphylococcus* positive serum | − | − | − | − | − |
| Chicken coccidiosis positive serum | − | − | − | − | − |
| Chicken taeniasis positive serum | − | − | − | − | − |
| Avian leukosis virus positive serum | − | − | − | − | − |
| Chicken newcastle disease positive serum | − | − | − | − | − |
| Avian influenza positive serum | − | − | − | − | − |
| Chicken Marek's disease positive serum | − | − | − | − | − |
| Chicken infectious bursal disease positive serum | − | − | − | − | − |
| Mycoplasma gallisepticum positive serum | − | − | − | − | − |
| Chicken egg drop syndrome positive serum | − | − | − | − | − |
| Avian encephalomyelitis virus infection positive serum | − | − | − | − | − |
| Chicken Infectious bronchitis virus positive serum | − | − | − | − | − |
| Yellow feather broiler (rooster) serum | − | − | − | − | − |
| Yellow feather broiler (hen) serum | − | − | − | − | − |
| White feather broiler (rooster) serum | − | − | − | − | − |
| White feather broiler (hen) serum | − | − | − | − | − |
| Hailan Brown commercial layer serum | − | − | − | − | − |
| Guangxi Yuanfeng spiced chicken (Lingshan fragrant chicken) serum | − | − | − | − | − |
| Changzhou Sandeli Golden Grass chicken serum | − | − | − | − | − |
| Jiangsu Lihua snow mountain chicken serum | − | − | − | − | − |
| Beijing fatty chicken serum | − | − | − | − | − |
| Xishuangbanna Yunling Chahua chicken serum | − | − | − | − | − |

TABLE 2-continued

Agglutination reaction test results of different concentrations of carrier bacteria S9 suspension with chicken sera

| | Carrier bacteria S9 bacteria suspension with different concentrations (cfu/mL) | | | | |
|---|---|---|---|---|---|
| | 500 million | 1 billion | 2 billion | 5 billion | 10 billion |
| Luhua chicken serum | − | − | − | − | − |
| Jiangsu Luyuan chicken Serum | − | − | − | − | − |

Note:
"−" represents negative;"+" represents positive

In summary, the basic principle of the invention of the present application, the main identification characteristics of the inert carrier bacteria S9, and an inert carrier provided by the inert carrier bacteria in the development of an indirect agglutination test detection method and potential application prospects are described. Those skilled in the art should understand that the present invention is not limited by the above embodiments, and the above embodiments and specification only describe the invention principles of the present application. Without departing from the functions, principles and scope of the present invention, the present invention will continue to be improved and perfected, and these improvements are required to be within the protection scope of the present invention. The claimed protection scope of the present invention is defined by the appended claims and equivalents thereof.

What is claimed is:

1. A method for detecting an antigen or an antibody in a biological sample, comprising:
   providing a *Salmonella* CGMCC17340 (deposited in the China General Microbiological Culture Collection Center under the accession number of CGMCC No. 17340) as an agglutination agent, and
   mixing the *Salmonella* CGMCC17340 with the biological sample and a specific antibody against the antigen, or mixing the *Salmonella* CGMCC17340 with the biological sample and a specific antigen interacted with the antibody,
   wherein the biological sample is chicken serum or chicken blood, and the antigen or the antibody result from a chicken-related pathogen infection.

2. The method according to claim 1, wherein the *Salmonella* CGMCC17340 is resuspended in PBS (Phosphate Buffered Saline) at a concentration of 500 million to 10 billion cfu/mL.

* * * * *

```
                        SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: It is synthesized.

<400> SEQUENCE: 1
aacagtcact ttgagcatgg gtt                                          23

<210> SEQ ID NO 2
<211> LENGTH: 22
<212> TYPE: DNA
<213> ORGANISM: Artificial Sequence
<220> FEATURE:
<223> OTHER INFORMATION: It is synthesized.

<400> SEQUENCE: 2
gagtgacttt gtctgctctt ca                                           22
```